United States Patent [19]
Anderson et al.

[11] Patent Number: 5,501,602
[45] Date of Patent: Mar. 26, 1996

[54] DENTAL CARE EDUCATIONAL AND TOOTH FAIRY VISIT KIT WITH MAGIC DUST

[76] Inventors: Karen L. Anderson; Keith E. Anderson, both of 247 Center Church Rd., McMurray, Pa. 15317

[21] Appl. No.: 325,978

[22] Filed: Oct. 21, 1994

Related U.S. Application Data

[63] Continuation-in-part of Ser. No. 25,497, Jul. 5, 1994, which is a continuation of Ser. No. 10,138, Jul. 1, 1993, abandoned.

[51] Int. Cl.$^6$ .................................................. G09B 23/28
[52] U.S. Cl. ........................ 434/263; 434/236; 434/433; 206/0.81; 206/229; 206/232; 206/83; 446/75; 446/491
[58] Field of Search .................................. 434/263, 236, 434/433; 206/83, 63.5, 579, 223, 229, 0.81, 232; 446/71–75, 491

[56] References Cited

U.S. PATENT DOCUMENTS

| | | |
|---|---|---|
| 3,638,785 | 2/1972 | Casteel et al. ............................ 206/229 |
| 4,091,481 | 5/1978 | Redman . |
| 4,372,077 | 2/1983 | Balbuena . |
| 4,777,745 | 10/1988 | Rose . |
| 4,888,251 | 12/1989 | Nakada ................................... 434/263 |
| 4,919,268 | 4/1990 | Young et al. . |
| 4,923,058 | 5/1990 | Dennison .................................. 206/83 |
| 5,015,209 | 5/1991 | Ortiz . |
| 5,050,729 | 9/1991 | Karbowniczak .......................... 206/83 |
| 5,086,547 | 2/1992 | Ziemelis . |
| 5,209,487 | 5/1993 | Rizzo .................................. 206/579 X |
| 5,244,394 | 9/1993 | Serabian-Musto ...................... 434/263 |
| 5,394,989 | 3/1995 | Delson . |

*Primary Examiner*—Robert A. Hafer
*Assistant Examiner*—Michael O'Neill

[57] ABSTRACT

A dental care kit for simulating a visit of a fictional tooth fairy and instructing a child of the importance of proper dental care. The inventive kit includes a storage chest containing a plurality of envelopes, magical fairy dust contained within a fairy dust container, an ink pad, left and right foot stamps, a coin bag, and a plurality of written notes. A method of utilizing the kit includes placing a deciduous tooth within one of the envelopes and underneath a pillow of the child's sleeping accommodations. After the child falls asleep, a parent of the child removes the tooth in the envelope for storage within the chest, sprinkles the magical fairy dust around and about the child, utilizes the left and right foot stamps and ink pad to place footprints on or about the child, places an amount of money within the coin bag underneath the pillow, and leaves one of the written notes underneath the pillow along with the coin bag. The fairy dust and footprints thus serve to convince the child of the existence of the fictional tooth fairy, while instructional indicia printed on the written notes instructs the child of the importance of proper dental care.

9 Claims, 4 Drawing Sheets

DENTAL CARE EDUCATIONAL AND TOOTH FAIRY VISIT KIT WITH MAGIC DUST

RELATED APPLICATION

This application is a continuation-in-part of application, Ser. No. 29/025,497, filed Jul. 5, 1994, which, in turn, is a continuation of prior application Ser. No. 29/010,138, filed Jul. 1, 1993, now abandoned.

Background of the Invention

1. Field of the Invention

The present invention relates to educational devices and more particularly pertains to for simulating a visit of a fictional tooth fairy and instructing a child of the importance of proper dental care.

2. Description of the Prior Art

The use of educational devices is known in the prior art. More specifically, educational devices heretofore devised and utilized are known to consist basically of familiar, expected and obvious structural configurations, notwithstanding the myriad of designs encompassed by the crowded prior art which have been developed for the fulfillment of countless objectives and requirements.

Known prior art educational devices include U.S. Pat. Nos. 5,015,209; 4,919,268; 5,086,547; 4,091,481; and 4,372,077.

While these devices fulfill their respective, particular objectives and requirements, the aforementioned patents do not disclose a dental care kit for simulating a visit of a fictional tooth fairy and instructing a child of the importance of proper dental care which includes a storage chest containing a plurality of envelopes, magical fairy dust contained within a fairy dust container, an ink pad, left and right foot stamps, a coin bag, and a plurality of written notes. Furthermore, none of the prior art teaches or suggests a method of utilizing the dental care kit which includes placing a deciduous tooth within one of the envelopes and underneath a pillow of the child's sleeping accommodations, removing the deciduous tooth in the envelope for storage within the chest, sprinkling the magical fairy dust around and about the child, utilizing the left and right foot stamps and ink pad to place footprints on or about the child, placing an amount of money within the coin bag and underneath the pillow, and placing one of the written notes underneath the pillow, wherein the fairy dust and footprints serve to convince the child of the existence of the fictional tooth fairy, with instructional indicia printed on the written notes instructing the child of the importance of proper dental care.

In these respects, the dental care educational kit according to the present invention substantially departs from the conventional concepts and designs of the prior art, and in so doing provides an apparatus primarily developed for the purpose of simulating a visit of a fictional tooth fairy and instructing a child of the importance of proper dental care.

SUMMARY OF THE INVENTION

In view of the foregoing disadvantages inherent in the known types of educational devices now present in the prior art, the present invention provides a new dental care educational kit construction wherein the same can be utilized for simulating a visit of a fictional tooth fairy and instructing a child of the importance of proper dental care. As such, the general purpose of the present invention, which will be described subsequently in greater detail, is to provide a new dental care educational kit apparatus and method which has many of the advantages of the educational devices mentioned heretofore and many novel features that result in a dental care educational kit which is not anticipated, rendered obvious, suggested, or even implied by any of the prior art educational devices, either alone or in any combination thereof.

To attain this, the present invention generally comprises a dental care kit for simulating a visit of a fictional tooth fairy and instructing a child of the importance of proper dental care. The inventive kit includes a storage chest containing a plurality of envelopes, magical fairy dust contained within a fairy dust container, an ink pad, left and right foot stamps, a coin bag, and a plurality of written notes. A method of utilizing the kit includes placing a deciduous tooth within one of the envelopes and underneath a pillow of the child's sleeping accommodations. After the child falls asleep, a parent of the child removes the tooth in the envelope for storage within the chest, sprinkles the magical fairy dust around and about the child, utilizes the left and right foot stamps and ink pad to place footprints on or about the child, places an amount of money within the coin bag underneath the pillow, and leaves one of the written notes underneath the pillow along with the coin bag. The fairy dust and footprints thus serve to convince the child of the existence of the fictional tooth fairy, while instructional indicia printed on the written notes instructs the child of the importance of proper dental care.

There has thus been outlined, rather broadly, the more important features of the invention in order that the detailed description thereof that follows may be better understood, and in order that the present contribution to the art may be better appreciated. There are, of course, additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Further, the purpose of the foregoing abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

It is therefore an object of the present invention to provide a new dental care educational kit apparatus and method which has many of the advantages of the educational devices mentioned heretofore and many novel features that result in a dental care educational kit which is not anticipated, rendered obvious, suggested, or even implied by any of the prior art educational devices, either alone or in any combination thereof.

It is another object of the present invention to provide a new dental care educational kit which may be easily and efficiently manufactured and marketed.

It is a further object of the present invention to provide a new dental care educational kit which is of a durable and reliable construction.

An even further object of the present invention is to provide a new dental care educational kit which is susceptible of a low cost of manufacture with regard to both materials and labor, and which accordingly is then susceptible of low prices of sale to the consuming public, thereby making such dental care educational kits economically available to the buying public.

Still yet another object of the present invention is to provide a new dental care educational kit which provides in the apparatuses and methods of the prior art some of the advantages thereof, while simultaneously overcoming some of the disadvantages normally associated therewith.

Still another object of the present invention is to provide a new dental care educational kit for simulating a visit of a fictional tooth fairy and instructing a child of the importance of proper dental care.

Yet another object of the present invention is to provide a new dental care educational kit which includes a storage chest containing a plurality of envelopes, magical fairy dust contained within a fairy dust container, an ink pad, left and right foot stamps, a coin bag, and a plurality of written notes.

Even still another object of the present invention is to provide a new dental care educational kit which includes a method of utilizing the kit comprising placing a deciduous tooth within one of the envelopes and underneath a pillow of the child's sleeping accommodations, removing the deciduous tooth in the envelope for storage within the chest, sprinkling the magical fairy dust around and about the child, utilizing the left and fight foot stamps and ink pad to place footprints on or about the child, placing an amount of money within the coin bag and underneath the pillow, and placing one of the written notes underneath the pillow, wherein the fairy dust and footprints serve to convince the child of the existence of the fictional tooth fairy, with instructional indicia printed on the written notes instructing the child of the importance of proper dental care.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there is illustrated preferred embodiments of the invention.

BRIEF DESCRIPTION OF THE DRAWINGS

The invention will be better understood and objects Other than those set forth above will become apparent when consideration is given to the following detailed description thereof. Such description makes reference to the annexed drawings wherein.

DESCRIPTION OF THE PREFERRED EMBODIMENT

Figure 1:
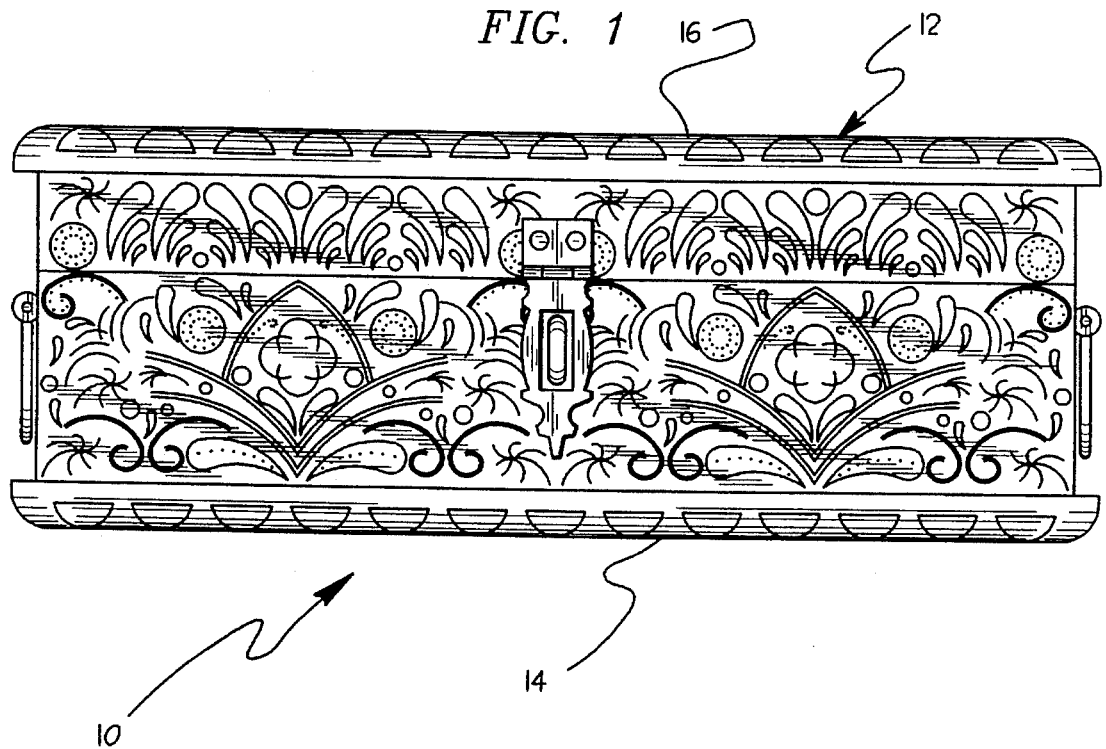
FIG. 1 is a front elevational view of a storage chest comprising a first component of the present invention.

With reference now to the drawings, and in particular to FIGS. 1–9 thereof, a new dental care educational kit embodying the principles and concepts of the present invention and generally designated by the reference numeral 10 will be described.

Figure 2:
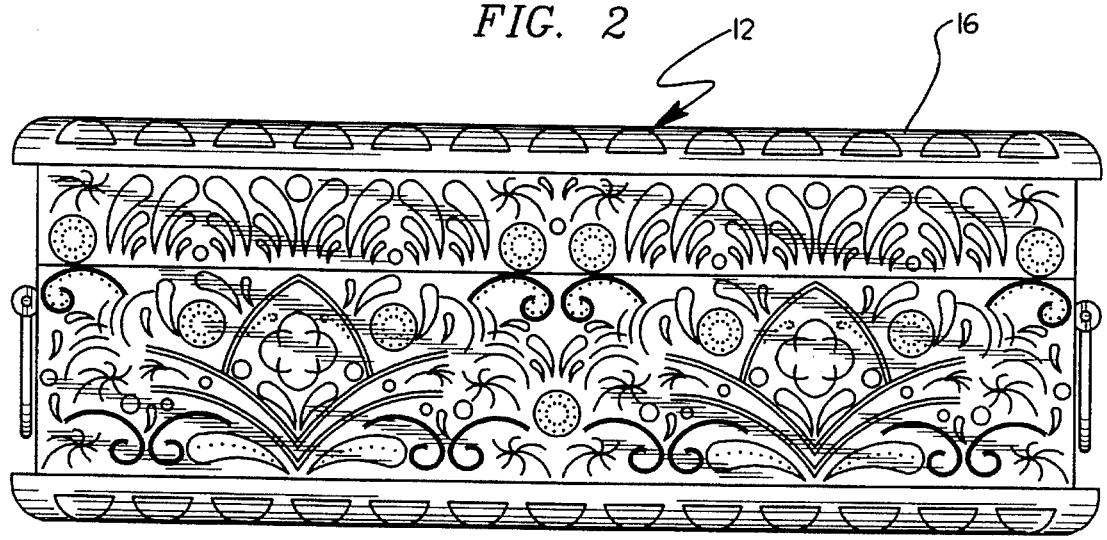
FIG. 2 is a top plan view of the storage chest.
Figure 3:
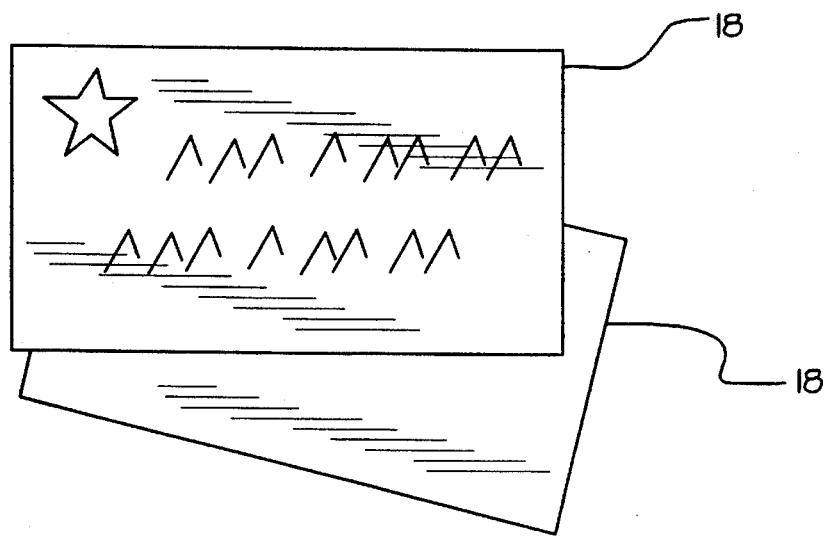
FIG. 3 is a top plan view of a plurality of envelopes comprising a second component of the present invention.
Figure 4:
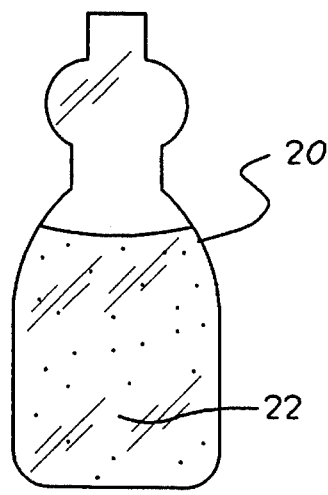
FIG. 4 is a front elevational view of a magical fairy dust container comprising a third component of the invention.
Figure 5:
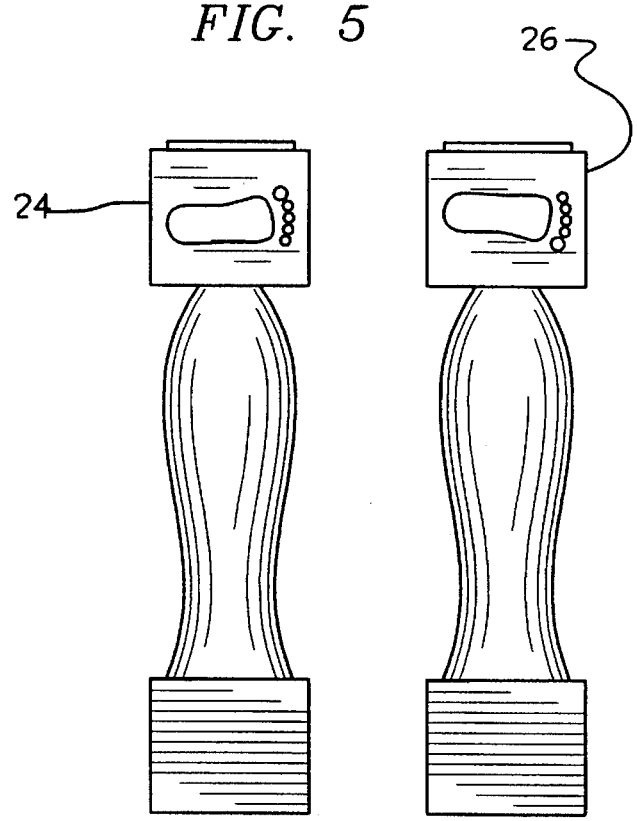
FIG. 5 is a front elevational view of left and right foot stamps comprising a fourth component of the present invention.
Figure 6:
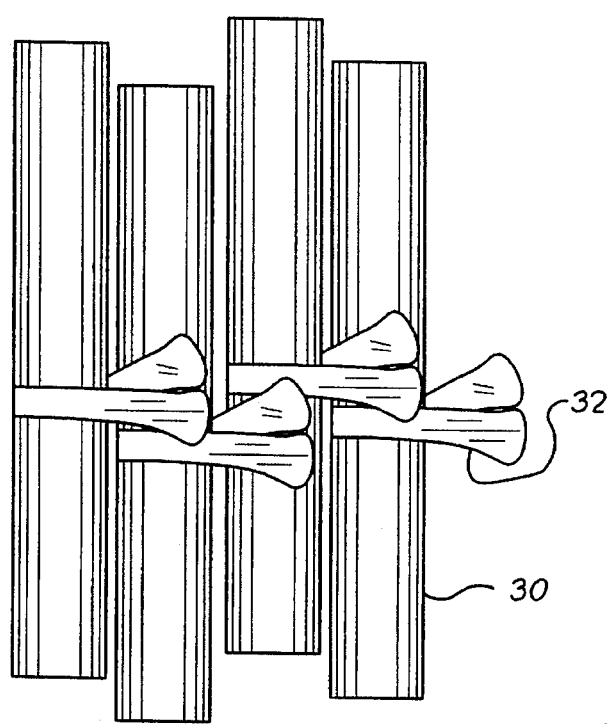
FIG. 6 is a top plan view of a plurality of written notes comprising a fifth component of the invention.
Figure 7:
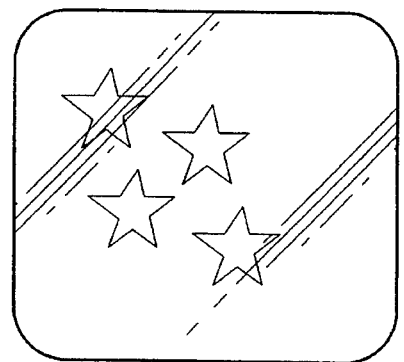
FIG. 7 is a top plan view of an ink pad comprising a sixth component of the present invention.
Figure 8:
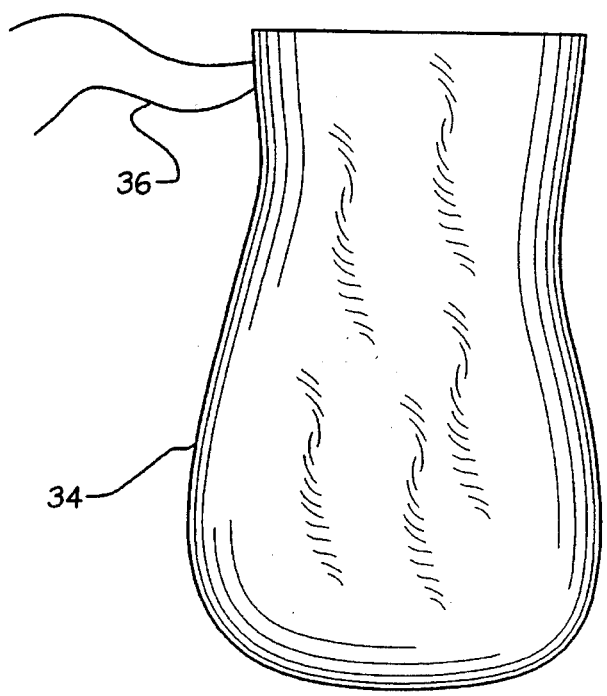
FIG. 8 is a front elevation view of a coin bag comprising a seventh component of the present invention.
Figure 9:
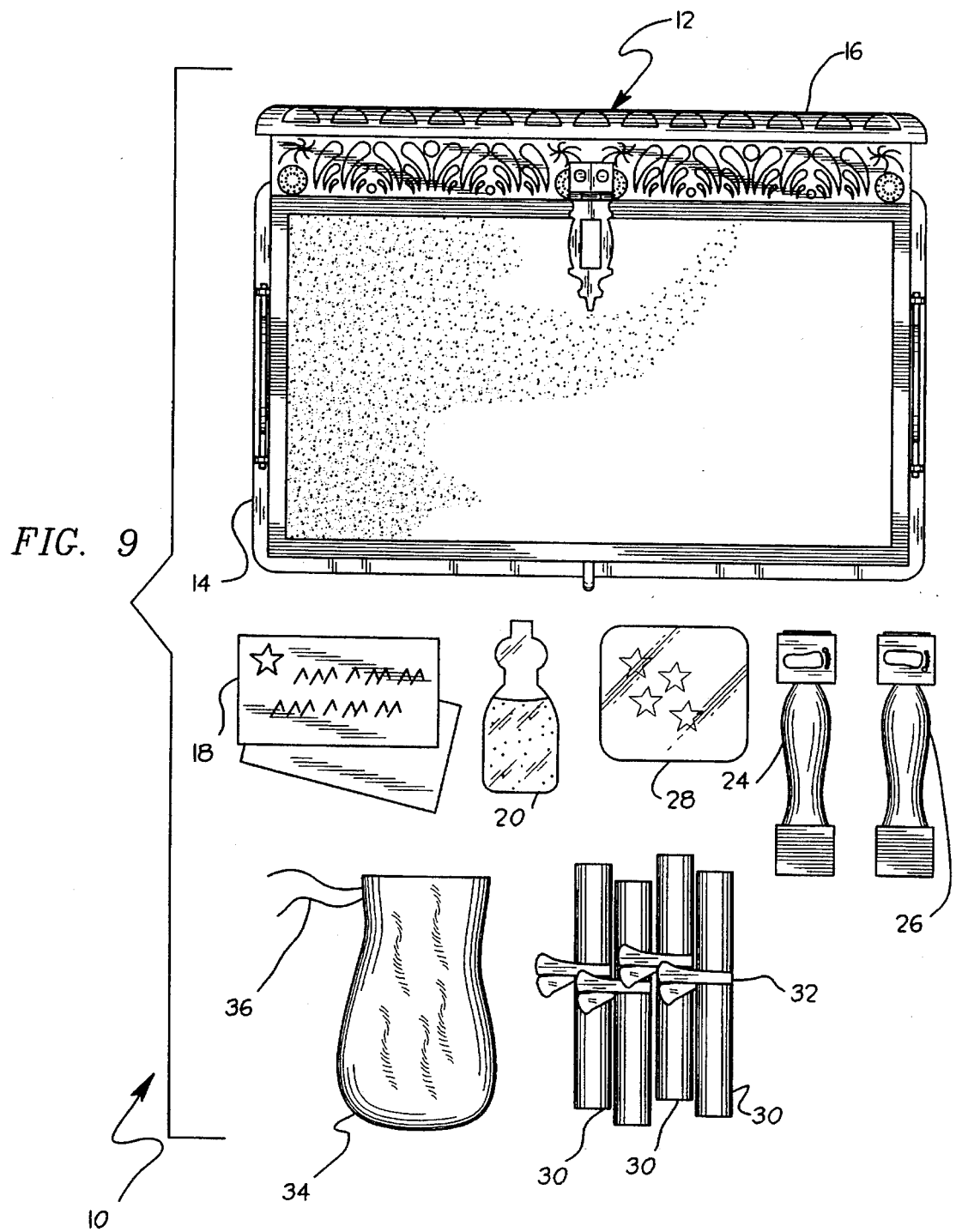
FIG. 9 is a plan view of the components of the present invention.

More specifically, it will be noted that the dental care educational kit 10 comprises a storage chest 12 having a rectangular main body 14 and a lid 16 pivotally coupled to the main body, as illustrated in FIGS. 1 and 2. FIG. 3 shows a plurality of envelopes 18 for receiving a deciduous tooth, i.e. a baby tooth, to be placed underneath an unillustrated pillow. Preferably, the kit 10 includes eight such envelopes for facilitating repeated use of the kit. A magical fairy dust container 20 shown in FIG. 4 contains a volume of magical fairy dust 22 and is configured to dispense the magical fairy dust in small amounts. Preferably, the magical fairy dust 22 comprises a metallic flake powder which exhibits reflective properties in the presence of light to enhance viewing of the fairy dust. FIG. 5 illustrates a left foot stamp 24 and a right foot stamp 26 which can be utilized with an ink pad 28 shown in FIG. 7 to create simulated left and right footprints on the child and surrounding bedding. The ink pad 28 desirably includes a water-based ink which can be easily washed from the bedding and the skin of the child after use of the kit 10. A plurality of written notes 30 are shown in FIG. 6, with each of the written notes being rolled into a closed cylindrical configuration and secured in the closed configuration by a securing ribbon 32 extending circumferentially about a center portion thereof. Lastly, a coin bag 34 having a drawstring closure 36 is shown in FIG. 8. The storage chest 12 is configured to receive all of the components 18–34 of the kit 10 for storage.

A method of utilizing the kit 10 is performed when a child first looses a deciduous or baby tooth. The lost tooth is placed within one of the envelopes 18 and positioned underneath a pillow of sleeping accommodations in which the child retires. The child is instructed to go to sleep and the lights are turned out. After the child falls asleep, a parent of the child removes the envelope 18 containing the tooth from underneath the pillow for storage within the storage chest 12. The parent then sprinkles the magical dust 22 from the container 20 onto the child and surrounding bedding. Footprints simulating the footprints of a fictional tooth fairy can then be created by placing the left and right foot stamps 24 and 26 into contact with the ink pad 28 to effect inking thereof, and subsequently stamping the footprints onto the child and surrounding bedding. Preferably, at least a few foot prints are placed onto the facial area of the child. A sum of money is placed within the coin bag 34, the draw string closure 36 is closed, and the coin bag is placed beneath the pillow in place of the envelope containing the deciduous tooth. Lastly, one of the written notes 30 is placed beneath the pillow for instructing the child of the importance of proper dental care.

When the child awakes in the morning, the child will discover the money left in the coin bag 34, the written note 30, the fairy dust 22, and the footprints printed about the child and the surrounding bedding which cooperate to convince the child of the existence of a magical tooth fairy named "Wishes". The instructional indicia printed on the written note 30 is then read by the child with more attentiveness and interest then in an absence of such convincing evidence, i.e. without the footprints, magical dust, and coin bag containing the sum of money. The method of instructing the child is especially useful in combination with a story relating to the method which details the purpose of the fictional fairy tooth character. An example of a story useful in communicating to the child is as follows:

> One day, a little boy named Kyle was having a tough day. His tooth was loose and nothing was going well because all Kyle could think of was wiggling his loose tooth with his finger and tongue. Then something special happened with one little push. Kyle's first tooth fell out. He was so excited he couldn't wait to tell his Mommy and Daddy.
>
> That night, Kyle's Mommy and Daddy helped him get his little baby tooth all ready. They put it in a little envelope and placed it under his pillow. Then Kyle asked, "Mommy, why are you putting my tooth under my pillow?" You will see Mommy said. "Tonight is a very special night. If you fall asleep soon enough, you will get a visit from a magical tooth fairy named Wishes. Now that you have your tooth under your pillow, as soon as you fall asleep, that will be Wishes' signal to come see you. "Oh hurry, Mommy, turn out the lights!" Kyle said, I can't wait for Wishes to come. I'm so excited!"
>
> "I can't wait either" said Mommy. "I am sure Wishes will be very excited to see you and your first missing tooth, Kyle."
>
> Mommy tucked Kyle in, kissed him goodnight, turned out the lights, and softly said, "I'11 see you in the morning Kyle."
>
> That night Kyle tossed and turned. Because he was so excited, it was really hard for him to fall asleep, but before he knew it, his Mom and Dad were by his side trying to wake him up, and it was morning.
>
> "Kyle! wake up . . . wake up! You're never going to believe what's all over your pillow!" Kyle could barely open his eyes when he realized there was magic dust and tiny little footprints all over his pillow. "Look Kyle, they're all over your cheeks and nose too!" Kyle ran over to his mirror and could not believe his eyes. Little footprints ran across his cheek and onto his nose. Kyle then ran back to his pillow. "Mommy, this can't be happening Under my pillow she left a small note and a little bag of coins." Kyle's Mommy opened the tiny note tied shut with a piece of ribbon while Kyle counted his coins. Then Kyle listened as she began to read the note:
>
> "Dear Sweet Little Kyle,
>
> My name is Wishes and I am your Tooth Fairy. Last night I flew through your window and landed on your pillow. Then I jumped right up on your cheek, walked across your face and stood right on your nose!
>
> I sprinkled magical fairy dust all over you! That made you yawn so big that was my chance to bend over and look right inside your mouth. I almost fell right in!
>
> What beautiful teeth you have. Now that you have lost your first tooth, this is a sign to really start taking extra, extra good care of them. You see, you only get two sets of teeth, and if the second one gets rotten and falls out, there's no third chances. You will have a missing tooth forever. So you must make sure that those bad nasty old sugarbugs don't get on your beautiful white teeth, especially your new one! They love to eat white clean teeth. So make sure you brush them off after every meal and ask your Mommy and Daddy what treats are good to eat. So take good care of them Kyle, and remember that because I sprinkled magical fairy dust all over you, all of your happy will come true. All you heave to do is think happy thoughts, and the way you want things to happen is they way they will. So when it seems like you are having a hard day and you're wishing things would get better, just remember to close your eyes, think happy thoughts, and thinks will start to go the way you want them to. Always believe in yourself Kyle. There is no one like you. See you soon."
> Wishes
>
> "Mommy, I love Wishes! She made me so happy. I can be anything I want to be when I grow up. Maybe one day I'll be a famous dentist and Wishes will be my assistant". Mommy said, "Yes, Kyle. Maybe some day you will be."
> THE END.

In use, the kit and method of the present invention serve to reinforce in the mind of the child the importance of proper dental care. Because the footprints are placed on the facial area of the child, the footprints may be left one the child's face the next day such that other children will be prompted to inquire as to the origin of the footprints. The repeated explanation of the origin of the footprints to other children throughout the next day will thus serve to further reinforce the story and associated instructional indicia printed on the written notes within the mind of the child.

As to a further discussion of the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed as being new and desired to be protected by Letters Patent of the United States is as follows:

1. A dental care educational kit comprising:

a storage chest;

an envelope for receiving a deciduous tooth;

a coin bag;

a magical fairy dust container; and magical fairy dust positioned within said container for dispensing therefrom, said magical fairy dust comprising a metallic flake powder which exhibits reflective properties in the presence of light to enhance viewing of said magical fairy dust.

2. The dental care educational kit of claim 1, and further comprising a left foot stamp and a right foot stamp which can be utilized for creating simulated left and right footprints, respectively; and an ink pad including a water based ink.

3. The dental care educational kit of claim 1, wherein said storage chest includes a rectangular main body and a lid pivotally coupled to said main body.

4. The dental care educational kit of claim 1, and further comprising a plurality of written notes, said written notes containing instructional indicia instructing a child of an importance of proper dental care.

5. The dental care educational kit of claim 4, wherein each of said written notes is rolled into a closed cylindrical configuration; and further comprising a plurality of ribbons securing said written notes in the closed cylindrical configuration, each of said ribbons extending circumferentially about a center portion of an individual one of said written notes.

6. A dental care educational kit comprising:

a storage chest;

an envelope for receiving a deciduous tooth;

a coin bag;

a left foot stamp and a right foot stamp which can be utilized for creating simulated left and right footprints, respectively; and an ink pad including a water based ink.

7. The dental care educational kit of claim 6, wherein said storage chest includes a rectangular main body and a lid pivotally coupled to said main body.

8. The dental care educational kit of claim 6, and further comprising a plurality of written notes, said written notes containing instructional indicia instructing a child of an importance of proper dental care.

9. The dental care educational kit of claim 8, wherein each of said written notes is rolled into a closed cylindrical configuration; and further comprising a plurality of ribbons securing said written notes in the closed cylindrical configuration, each of said ribbons extending circumferentially about a center portion of an individual one of said written notes.

* * * * *